United States Patent [19]

McKinlay

[11] Patent Number: 4,958,522
[45] Date of Patent: Sep. 25, 1990

[54] SHEAR STIFFNESS TESTER

[75] Inventor: Peter R. McKinlay, South Melbourne, Australia

[73] Assignee: Amcor Limited, South Melbourne, Australia

[21] Appl. No.: 307,411

[22] Filed: Feb. 6, 1989

[30] Foreign Application Priority Data

Feb. 10, 1988 [AU] Australia .................. PI6679

[51] Int. Cl.⁵ .............................. G01N 3/22
[52] U.S. Cl. ................................... 73/847
[58] Field of Search ............... 73/159, 847, 848, 849, 73/851, 853, 854; 493/37

[56] References Cited

U.S. PATENT DOCUMENTS

| | | | |
|---|---|---|---|
| 1,559,466 | 10/1925 | Schopper | 73/853 |
| 2,044,411 | 6/1936 | Vaughan, Jr. | 73/854 |
| 2,765,655 | 10/1956 | Scott | 73/847 |
| 2,960,863 | 11/1960 | Weiss | 73/847 |
| 3,122,915 | 3/1964 | Haller | 73/847 |
| 3,675,475 | 7/1972 | Weinstein | 73/847 |

FOREIGN PATENT DOCUMENTS

| | | | |
|---|---|---|---|
| 0096334 | 2/1898 | Fed. Rep. of Germany | 73/847 |
| 2745182 | 4/1979 | Fed. Rep. of Germany | 73/853 |
| 0171623 | 5/1966 | U.S.S.R. | 73/847 |
| 0449281 | 11/1974 | U.S.S.R. | 73/847 |
| 0640178 | 12/1978 | U.S.S.R. | 73/847 |

Primary Examiner—Robert Raevis
Attorney, Agent, or Firm—Bucknam and Archer

[57] ABSTRACT

A method and apparatus for determining structural properties of corrugated paperboard in which a sample 21 is held between two axially aligned jaws 13 and 14. The sample is subjected to a twisting force by rotation of one of the jaws and the force and angle of deflection are measured. This gives a relative determination of the boards structural property and is used to assess damage to the corrugated medium during corrugation and subsequent processing steps such as printing. The determination of shear stiffnes in the machine direction is a more reliable measure of board damage than board thickness.

4 Claims, 7 Drawing Sheets

SHEAR STIFFNESS TESTER

This invention relates to an instrument and method for testing paperboard products and assessing the structural properties of paperboard during manufacture. In particular, this invention is concerned with measuring shear stiffness of the corrugating medium in corrugated paperboard.

Measurement of shear stiffness provides an important parameter in defining the structural properties of paperboard and for determining the strength of corrugated paperboard panels for end use applications.

Various methods have been investigated for measuring the core (medium) shear stiffness of corrugated board. The methods currently used are:

(1) Three point beam test at various spans;
(2) Direct shear.

The first of these methods requires a lot of testing and for relatively stiff cores can give low results due to local buckling at the point of application of the central load.

The second method requires attaching the specimen to a rigid backing strip by gluing or some other means. This procedure is tedious and the results from this method are very variable due to the very small deflections involved during measurement.

BRIEF SUMMARY OF THE INVENTION

It is an object of this invention to provide a simpler method of determining shear stiffness using a few samples and to provide a device for carrying out the method.

In another aspect this invention relates to a method of assessing damage to corrugated board mediums during printing and box manufacture.

At present the recommended method of assessing medium damage is by thickness measurements of the board in accordance with 1987 Tappi Report 30304-11.

This invention provides a more accurate measure of medium damage by measuring medium shear stiffness in the machine direction.

To this end the present invention provides a method of testing corrugated paperboard as an aid in corrugated paperboard processing operations, in which a rectangular sample of corrugated paperboard is subjected to a controlled twisting force and a measure taken of the twisting force at a given angle of twist, a relative measure of structural properties of the board.

The method of this invention derives from the fact that a fundamental relationship exists between the shear stiffness of the core of a board and its stiffness to twisting.

By twisting a sample, shear strains are produced in the core.

By twisting a sample the following can be recorded:
(i) the initial angle of twist for a given load;
(ii) the change in the angle of twist over time under a constant load;
(iii) the force required to achieve an initial angle of twist;
(iv) the changes over time in the force required to maintain a given angle of twist.

The measurements can also be made with varying conditions of humidity and varying degrees of crush applied to the sample to determine performance of the medium under varying conditions.

By assessing a range of products it is possible to establish a scale of performance with small deflections for a given force or large forces to achieve a given deflection being the desirable characteristics of better quality paperboards.

The device useful in carrying out this invention essentially comprises a pair of axially aligned clamps at least one clamp being pivoted for rotation in a plane perpendicular to the alignment axis and means for measuring the force applied to rotate one of said clamps and means for measuring the angle of rotation.

The device can be manually operable with the addition of weights to a lever arm or the like to produce rotation of one clamp relative to the other. Alternatively, the device can be mounted on a force measuring instrument such as an INSTRON and the rotatable clamp moved to a constant maximum angle of rotation with measurement of the force required to achieve this result. Such a measurement can be repeated serially to determine the performance of the sample under such repetitive twist over time.

The method of this invention is used to measure shear stiffness in the Machine Direction (MD) of corrugated board. This means that the flutes are visible along the longside of the sample. This measure of MD shear measures approximately 80% of the required property and although not a pure measurement has great experimental advantages.

The various types of readings which can be gained provide a number of means of assessing the decay in shear stiffness over time as well as an initial assessment of shear stiffness. This enables a consistent comparison to be made of the quality of paperboard being produced or being utilised.

Thus, it can be used not only to assess the quality of board at a particular time but to also assess its likely behaviour in various humidities or after crushing to varying degrees.

BRIEF DESCRIPTION OF THE DRAWINGS

A preferred form of this invention will now be described with reference to the drawings in which.

Figure 1:
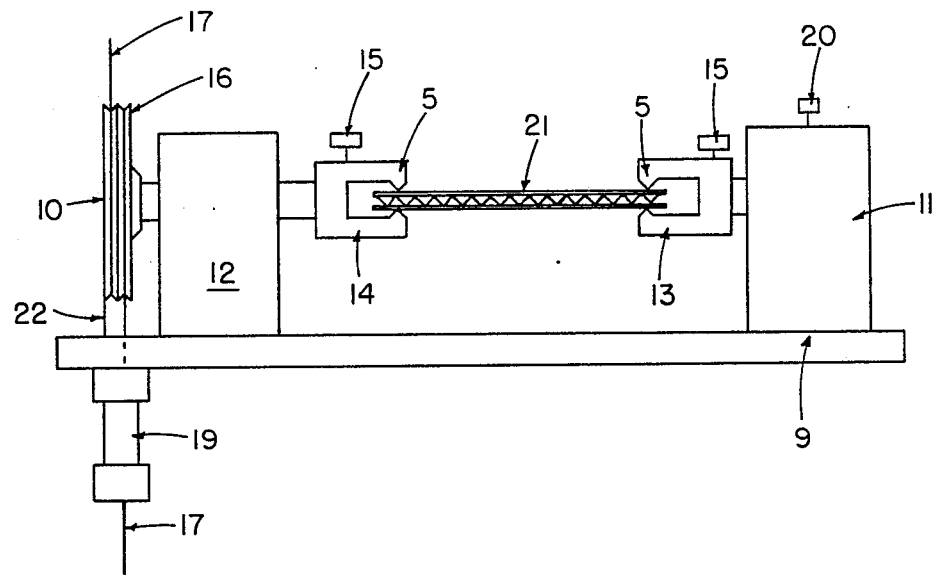
FIG. 1 is a schematic side view of a simple mechanical form of the device and FIG. 2 is an end view.

The device comprises a base 9, two axial supports 11 and 12 which support clamping heads 13 and 14 on a common axis 10. The clamping heads 13 and 14 are both rotatable in a plane perpendicular to the axis 10.

The sample to be tested is held with its longitudinal axis aligned with axis 10 in the clamps 13 and 14. Screws 15 enable clamps 13 and 14 to be tightened to effectively grip the sample 21 without producing out of balance in the clamps.

Clamp 13 can be fixed in position by preventing rotation of the pivot 10 connecting clamp 13 to the axial support 11 by way of adjustment screw 20.

Clamp 14 which is on a common axis with the wheel 16 is finely balanced to freely turn its axis.

Figure 2:
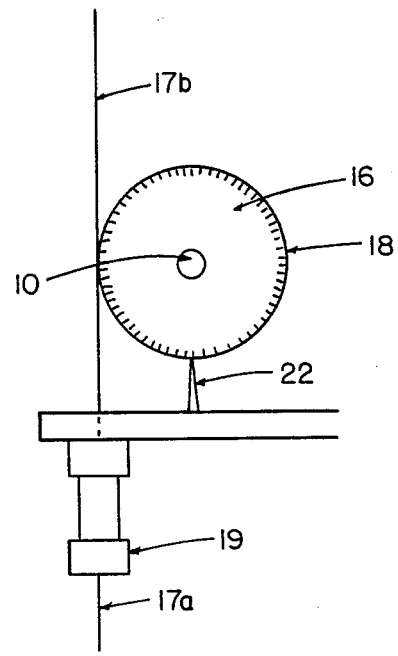

The wheel 16 can have a wire 17a wound onto it to support a weight hanging freely below the device. In this case wire 17b is not used, as shown in FIG. 2. The wheel 16 is marked with an angular scale 18 and the marker 22 is used to align the axis with the beginning of the scale.

To carry out testing, a specimen board is cut into test pieces of normal test size 100 mm by 25 mm.

A test piece 21 is then mounted into the clamp and the clamps 13 and 14 tightened. The clamps are rotated to bring the beginning of the scale 18 into alignment with marker 22 and the clamp 13 is fixed by tightening screw 20.

Figure 3:
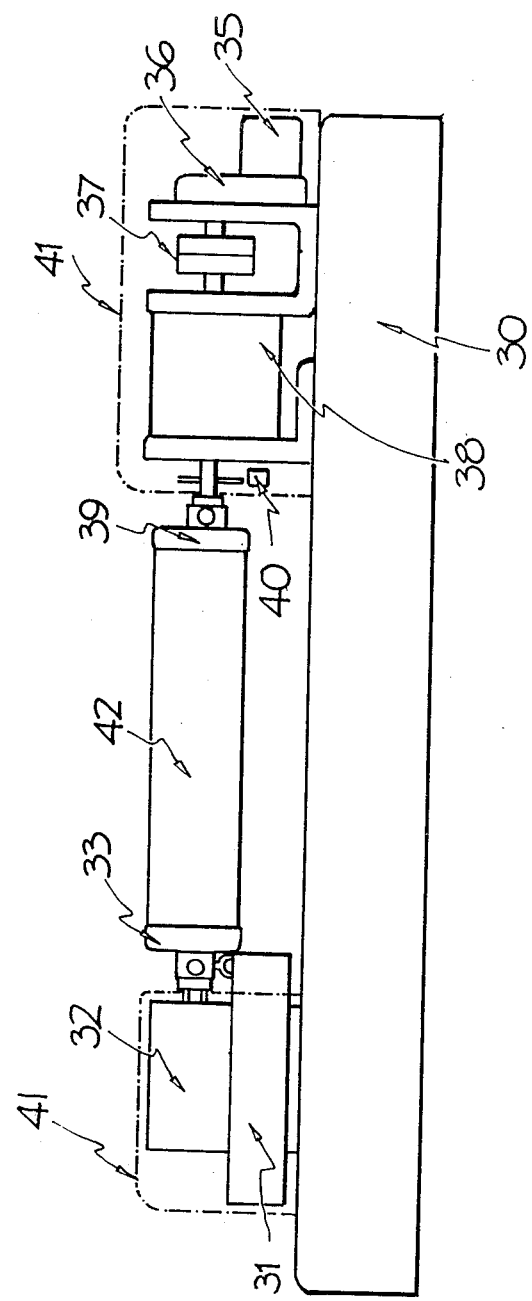
FIG. 3 is a schematic view of a form of device with microprocessor controls and digital display.

The embodiment shown in FIG. 3 comprises a base 30 supporting the instrument which comprises (i) a load cell 31 and its associated bearing housing 32 for the sample jaws 33.

(ii) an electric motor 35 and associated gearbox 36 connected via the coupling 37 to the rotary encoder 38 to which the sample jaws 39 are connected.

A cam and microswitch 40 are located between the sample jaw 39 and rotary encoder 38. The covers 41 enclose the stationary parts of the apparatus so that only the sample 42 and the jaws 33 and 39 are exposed.

Figure 4:
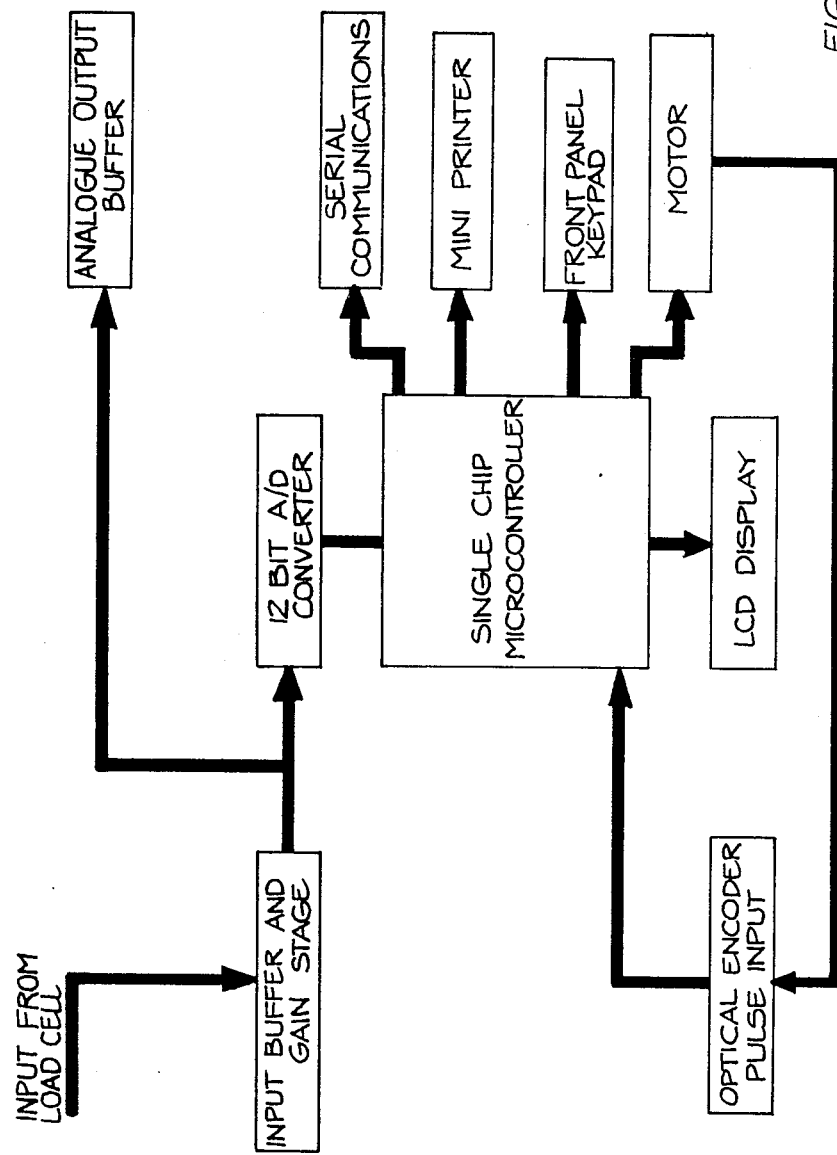
FIG. 4 is a block diagram of such a device.

This form of the testing device is microprocessor controlled as illustrated in the block diagram of FIG. 4. Inputs are received from the load cell and the rotary encoder to measure force and angular displacement.

The load cell measures the force. The rotary (optical) encoder measures (encodes) the rotation of the jaw to which it is physically connected. The encoded result is read by a micro controller for conversion to degree rotation. The block diagram in FIG. 4 indicates the fact that the micro controller controls rotation by driving the motor forward or backward during the testing sequence as required. Desired loads or angular deflections for samples can be keyed in. Readouts of force or displacement are shown on a LCD display panel. The electronic circuitry and the programming of the microprocessor are conventional.

Either apparatus can be operated in a number of modes to measure:

initial deflection under constant load
initial load for a constant deflection and
variations of these over time in either fixed or varying atmospheric and humidity conditions.

The symbol M designates the twisting motion and is the torque.

Figure 5:
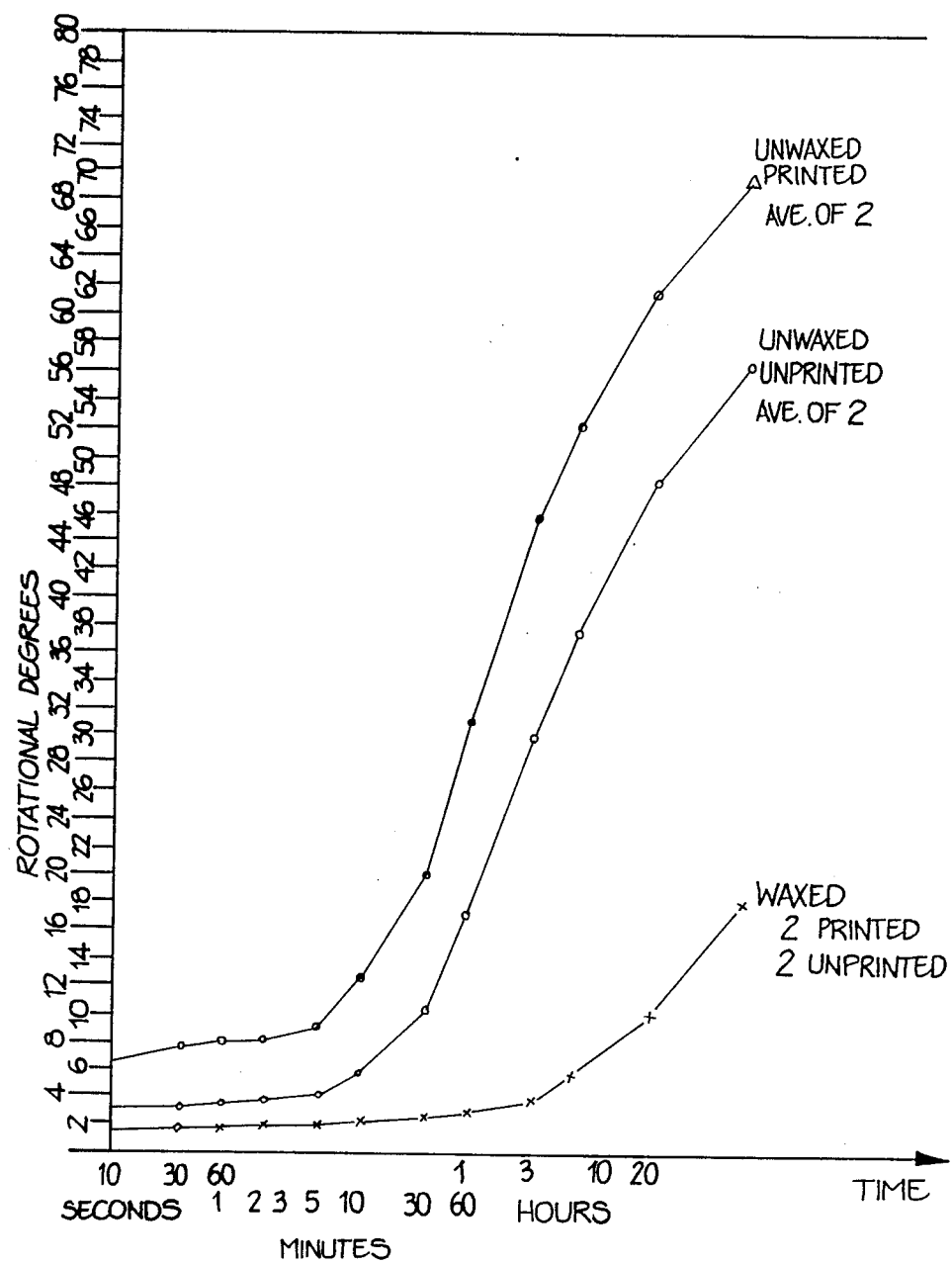
FIGS. 5, 6 and 8 are graphical results using the method of this invention.

The twisting movement (M) at the 13, 14 is proportional to the angle of jaw rotation theta and the MD Shear stiffness (S) of the corrugated sample. The constant of proportionality (K) is related to the geometry of the sample, namely its width (2a) (a being half the sample width with the corrugations transverse to the axis of rotation), and the geometry of the apparatus, namely the free length >(L) between the jaws 13, 14. That is: $M = K\theta S$ where $K = 4a^3/3L$ FIG. 5 shows the average performance of samples of waxed, unwaxed, unprinted and unwaxed printed boards over time under constant stress. The graphs illustrate the increase in deflection over time and demonstrate the superior shear stiffness of the waxed boards.

Comparative tests have been carried out to compare the industry recommended method of measuring medium damage with the method according to this invention.

Tests were carried out on samples from corrugated board used in making boxes in accordance with the following specifications:

Box Description

| | |
|---|---|
| Style: | M45T Red Seal<br>Regular Top and Bottom |
| Board Grade: | R284C |
| Construction: | 130/130-120/C |
| Sheet Size: | 1665 × 781 |

Machine Settings

| Corrugator | |
|---|---|
| Speed | 180 m/min, 115 m/min |
| Printer/Slotter | |
| Machine: | ZLM 1 |
| Speed: | 150 Sheets/min |

Machine Settings

| | |
|---|---|
| 1 Feed Roll | 90 |
| Pressure Roll | 240 |
| 2 Printing Cylinder | 1.5 |
| Pressure Roll | 150 |
| Printing Cylinder | 9 |
| 3 Die Cut Cylinder | 180 |
| 4 Delivery Section | 140 |

Figure 6:
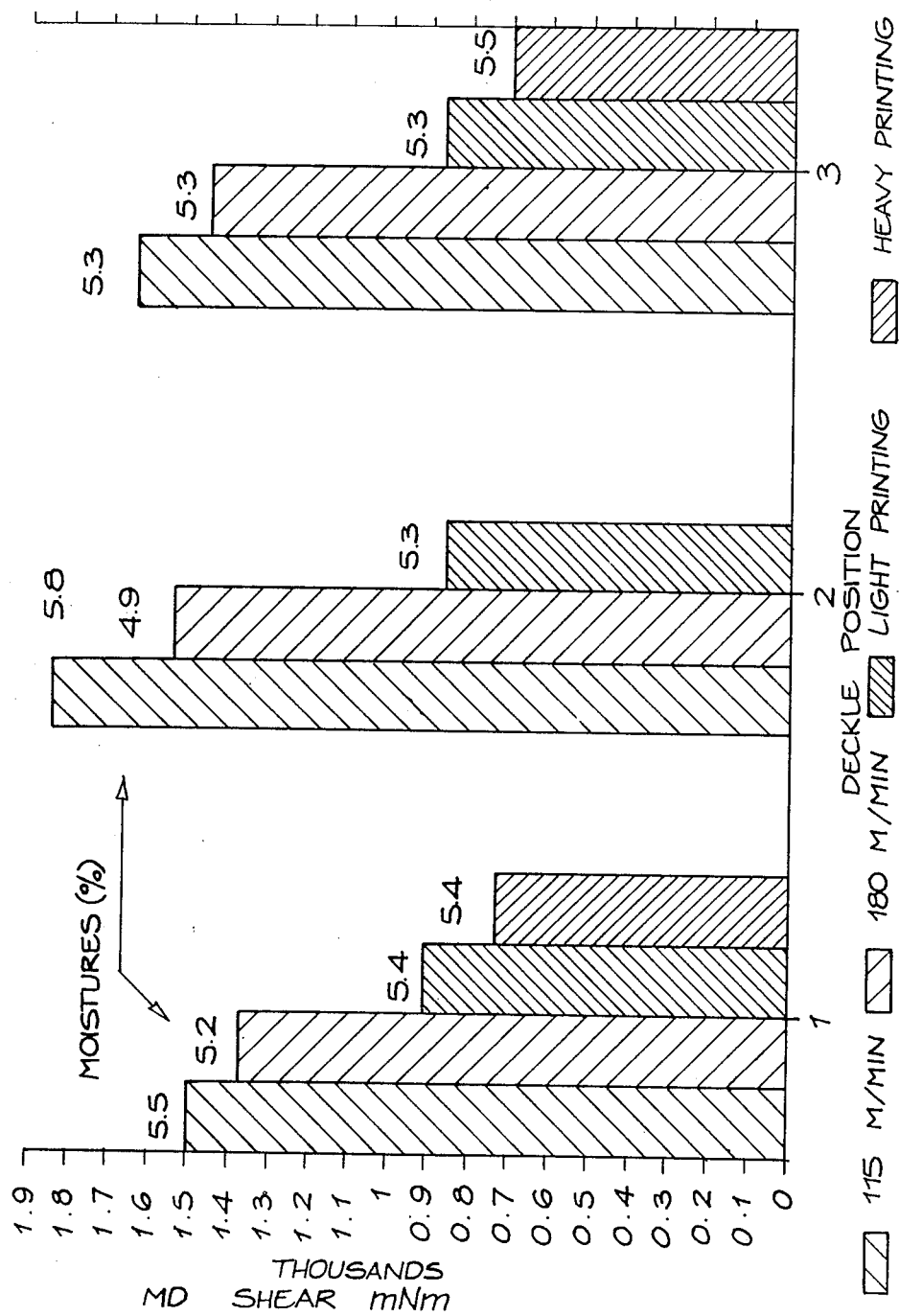
Figure 7:
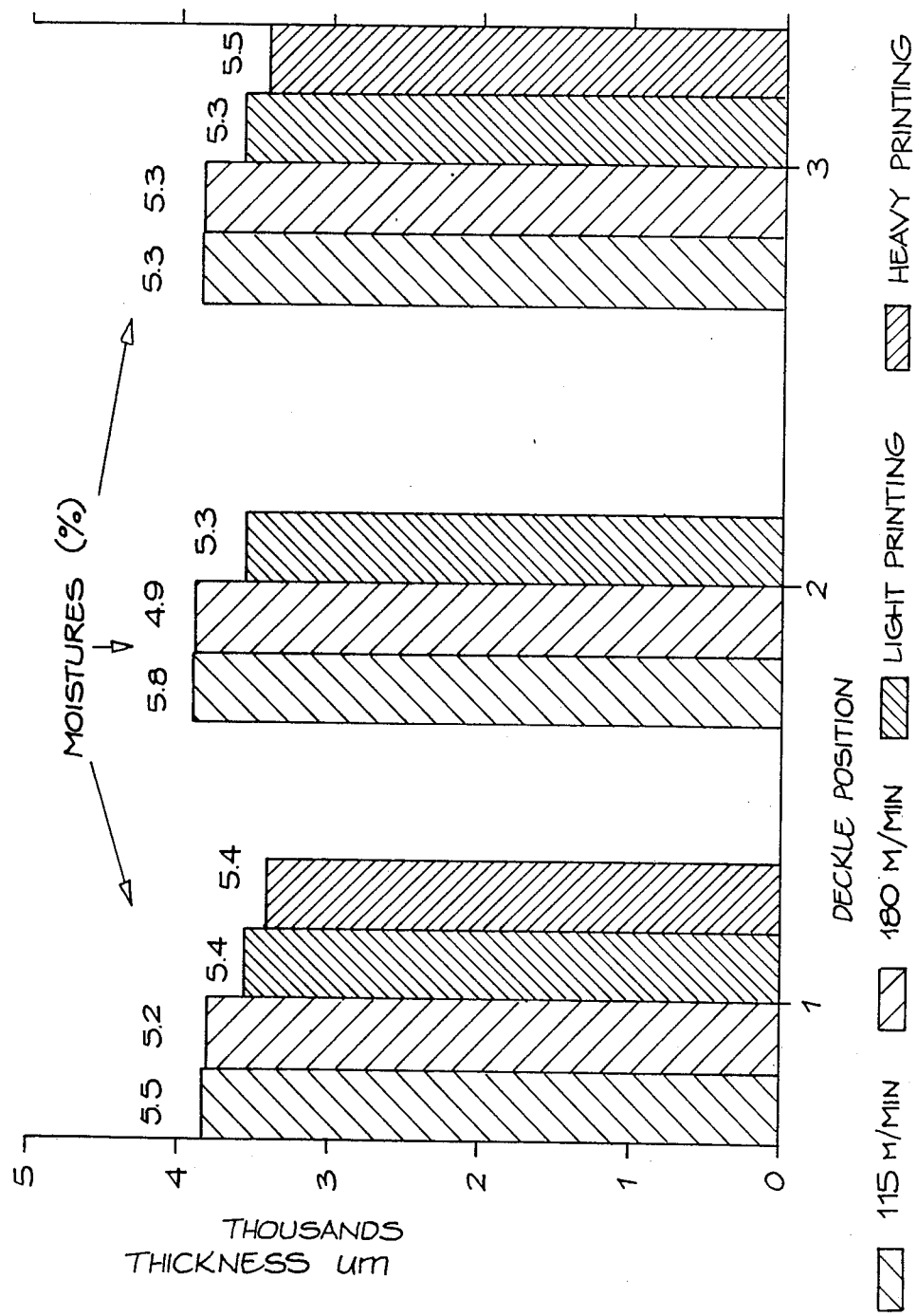
FIG. 7 is a graphical result for a prior art method.

FIG. 6 shows the load readings for shear stiffness measured in Milli Newton meters in accordance with the present invention and FIG. 7 shows the thickness of the same board.

A comparison of FIGS. 6 and 7 clearly shows that a much better measure of the board damage at various moisture levels in the board can be ascertained from Shear Stiffness measurements than from thickness. This is probably due in part to thickness recovery after damage has occurred.

Figure 8:
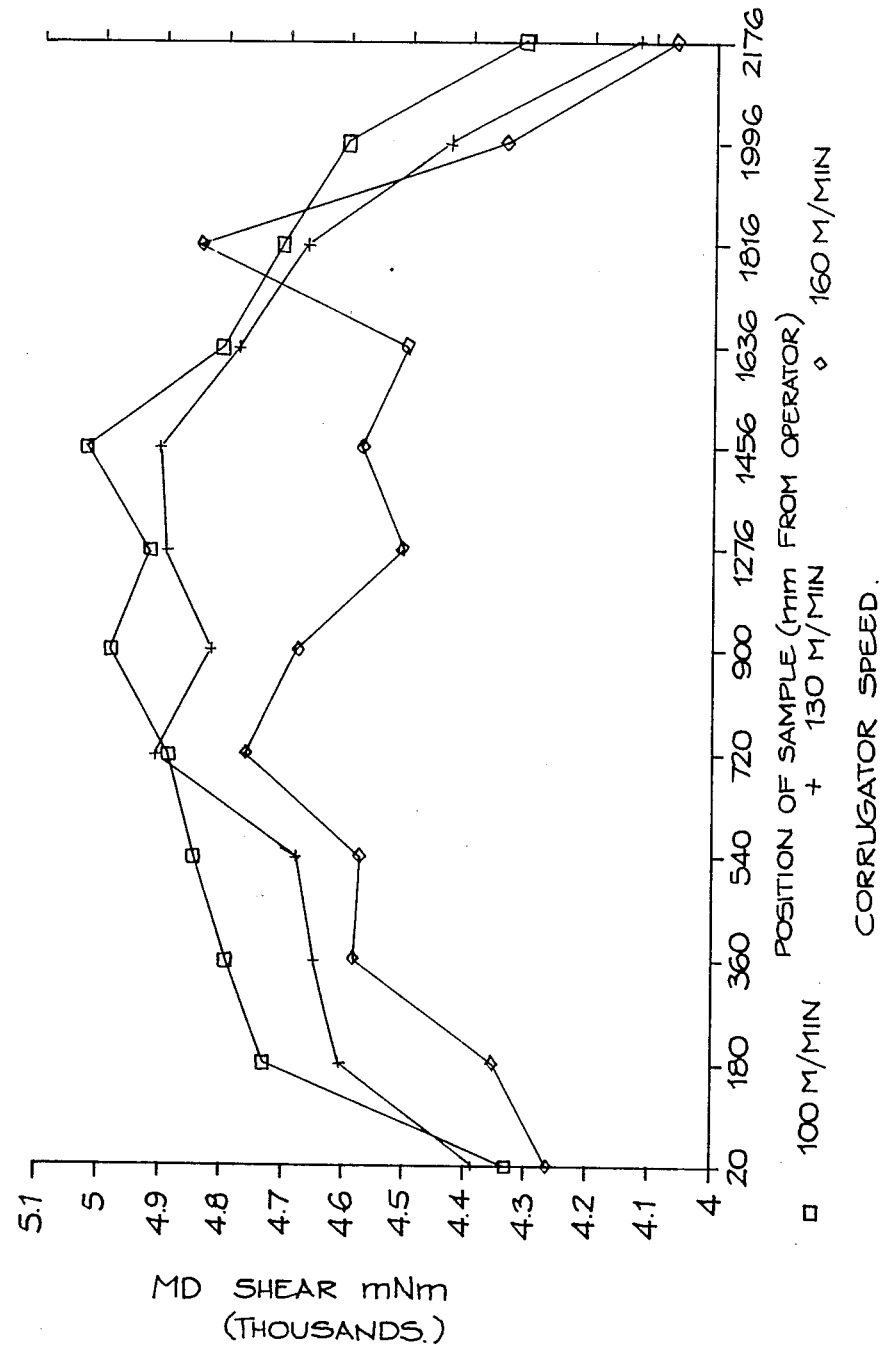

FIG. 8 illustrates another application of the present invention in assessing damage for quality control purposes across the corrugator machine.

By measuring the medium shear across the width of a corrugator a profile of the machine's effect on board quality is shown for different corrugator speeds.

The information derived from tests of the sort illustrated in FIGS. 6 and 8 enable operators to adjust machine speed or other operating conditions to maintain desired structural properties in the corrugated board.

Although the measurement of shear stiffness by this method is not a "pure" measurement it has experimental advantages. The apparatus is simple to use and requires minimal sample preparation.

I claim:

1. A method of determining the shear stiffness of corrugated paperboard as an aid in processing corrugated paperboard, consisting of subjecting a sample of corrugated paperboard to a twisting force and a) measuring the initial angle of twist for a given load; or b) measuring the change in the angle of twist over time under a constant load; or c) measuring the force required to achieve an initial angle of twist; or d) measuring the change over time in the force required to maintain a given angle of twist and wherein a sample of said corrugated paperboard is placed between two jaws and the Shear stiffness (S) is determined according to the equation $M = K\theta$ wherein M is the twisting torque, $\theta$ is the angle of jaw rotation and K is the proportionality constant $K = 4a^3/3L$ wherein a = width of the sample and L is the distance between said jaws.

2. The method according to claim 1 wherein the sample is rectangular in shape and held lengthwise by clamps located at each end and one end only is subjected to a twisting force.

3. The method according to claim 2 wherein the clamps are axially aligned and one clamp is pivoted for rotation in a plane perpendicular to the alignment axis.

4. The method according to claim 3 wherein the force needed to rotate said one clamp is measured and the angle of rotation of said one clamp is also measured.

* * * * *